US00PP19824P2

(12) United States Plant Patent
Avent

(10) Patent No.: US PP19,824 P2
(45) Date of Patent: Mar. 10, 2009

(54) *DIANTHUS* PLANT NAMED 'WICKED WITCH'

(50) Latin Name: *Dianthus gratianopolitanus*
Varietal Denomination: Wicked Witch

(76) Inventor: Tony Avent, 9241 Saul's Rd., Raleigh, NC (US) 27803

( * ) Notice: Subject to any disclaimer, the term of this patent is extended or adjusted under 35 U.S.C. 154(b) by 0 days.

(21) Appl. No.: 11/895,240

(22) Filed: Aug. 24, 2007

(51) Int. Cl.
*A01H 5/00* (2006.01)

(52) U.S. Cl. ..... Plt./272
(58) Field of Classification Search ..... Plt./272
See application file for complete search history.

(56) References Cited

PUBLICATIONS

Plant Delights Nursery, Inc. *Dianthus* 'Wicked Witch'[online][retrieved on Jun. 7, 2008], retrieved from the Internet at <http://www.plantdelights.com> one page.*

Plants for Europe Limited. PFE announces two new plants in portfolio. Feb. 16, 2005, [online][retrieved on Jun. 7, 2008], retrieved from the Internet at <http://www.plantsforeurope-.com/categories/new–plants//> 7 pages.*

Contact PFE [online][retreived on Jun. 9, 2008], retrieved from the Internet at <http://www.plantsforeurope.com/contact–pfe/> 3 pages.*

* cited by examiner

*Primary Examiner*—Annette H Para
*Assistant Examiner*—June Hwu

(57) ABSTRACT

A new cultivar of *Dianthus* plant named 'WICKED WITCH' that is characterized by pronounced compact habit, narrow grey-green foliage, and bright cherry-red flowers. In combination these traits set 'WICKED WITCH' apart from all other existing varieties of *Dianthus* known to the inventor.

2 Drawing Sheets

Genus: *DIANTHUS.*
Species: *gratianopolitanus*
Denomination: 'WICKED WITCH'.

BACKGROUND OF THE INVENTION

The present invention relates to a new and distinct cultivar of carnation or hardy pink that is grown for use as a flowering plant for pots and containers and for planting in the garden or landscape. The new cultivar is known botanically as *Dianthus gratianopolitanus* and will be referred to hereinafter by the cultivar name of 'WICKED WITCH'.

'WICKED WITCH' arose as a naturally occurring whole plant sport which the inventor discovered growing in a cultivated border in April 2002 at the inventor's nursery in Raleigh, N.C. The plant had been established while juvenile and nonflowering as the pink-flowered variety *Dianthus gratianopolitanus,* 'Feuerhexe' (not patented). 'Feuerhexe' is commonly known in the United States by its translated equivalent 'Firewitch'. The observed plant bore red flowers and the inventor determined that this observed plant was clearly distinguishable from 'Feuerhexe' by its flower color.

'WICKED WITCH' exhibits pronounced dense compact habit, blue-green foliage, and rich magenta flowers. It blooms profusely in the spring with a second bloom in the fall. The foliage forms a dense mat spreading to 15 cm to 20 cm in height and width.

'WICKED WITCH' differs from its parent plant in the color of its petals. The petals of 'Feuerhexe' are colored bright pink at maturity. The petals of 'WICKED WITCH' are colored red-purple at maturity. Like its parent 'Feuerhexe', 'WICKED WITCH' shares extreme durable and landscape toughness forming dense highly branched mats of foliage which endure during periods of excessive summer heat. 'WICKED WITCH' also closely resembles *Dianthus* 'Red Dwarf' (U.S. Pat. No. 14,437) and *Dianthus* 'Devon Xera' (U.S. Pat. No. 14,895). However, the petal colors of 'WICKED WITCH' fall into the red-purple class while 'Red Dwarf' and 'Devon Xera' are classified as red.

Asexual reproduction of 'Wicked Witch' was first accomplished by the inventor in 2004 in a cultivated area of Raleigh, N.C. The method of asexual propagation used was basal shoot cuttings. Since that time the characteristics of the new cultivar have been determined stable and are reproduced true to type in successive generations of asexual reproduction.

SUMMARY OF THE INVENTION

The following traits have been repeatedly observed and represent the characteristics of the new *Dianthus* cultivar 'WICKED WITCH'. These traits in combination distinguish this cultivar from all other commercial varieties known to the inventor. 'WICKED WITCH' has not been tested under all possible conditions and phenotypic differences may be observed with variations in environmental, climatic and cultural conditions, however, without any variance in genotype.

1. *Dianthus* 'WICKED WITCH' exhibits a pronounced compact habit.
2. *Dianthus* 'WICKED WITCH' blooms profusely and repeatedly.
3. *Dianthus* 'WICKED WITCH' exhibits rich magenta flowers.
4. *Dianthus* 'WICKED WITCH' exhibits blue-green foliage.
5. At maturity, the height and width of the foliage mound of *Dianthus* 'WICKED WITCH' ranges from 15 cm to 20 cm.

6. *Dianthus* 'WICKED WITCH' is a perennial which is hardy to USDA Zone 3.
7. *Dianthus* 'WICKED WITCH' is suitable for use as a flowering plant in pots and containers.

BRIEF DESCRIPTION OF THE DRAWINGS

The accompanying color drawings illustrate the overall appearance of the new *Dianthus* variety 'WICKED WITCH' showing colors as true as it is reasonably possible to obtain in colored reproductions of this type. Colors in the drawings may differ from the color values cited in the detailed botanical description, which accurately describe the actual colors of the new variety 'WICKED WITCH'.

The drawing labeled as FIG. 1 depicts an entire flowering plant at approximately 6 months.

Figure 1:
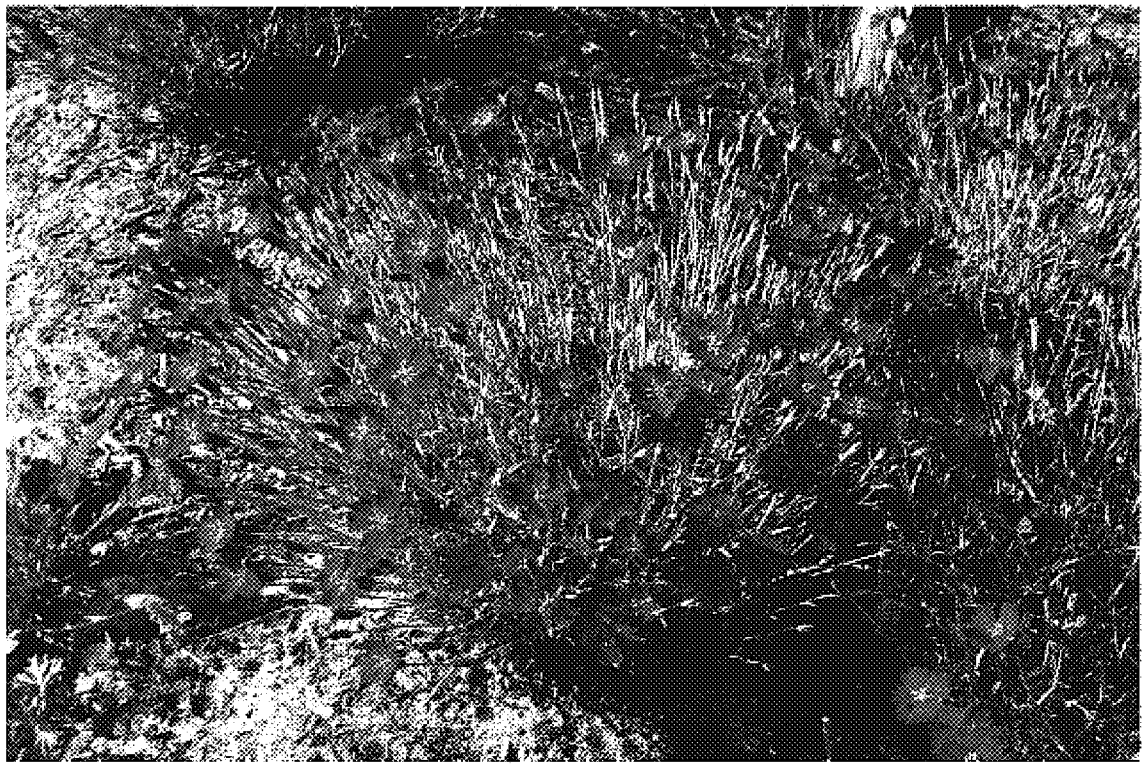
Figure 2:
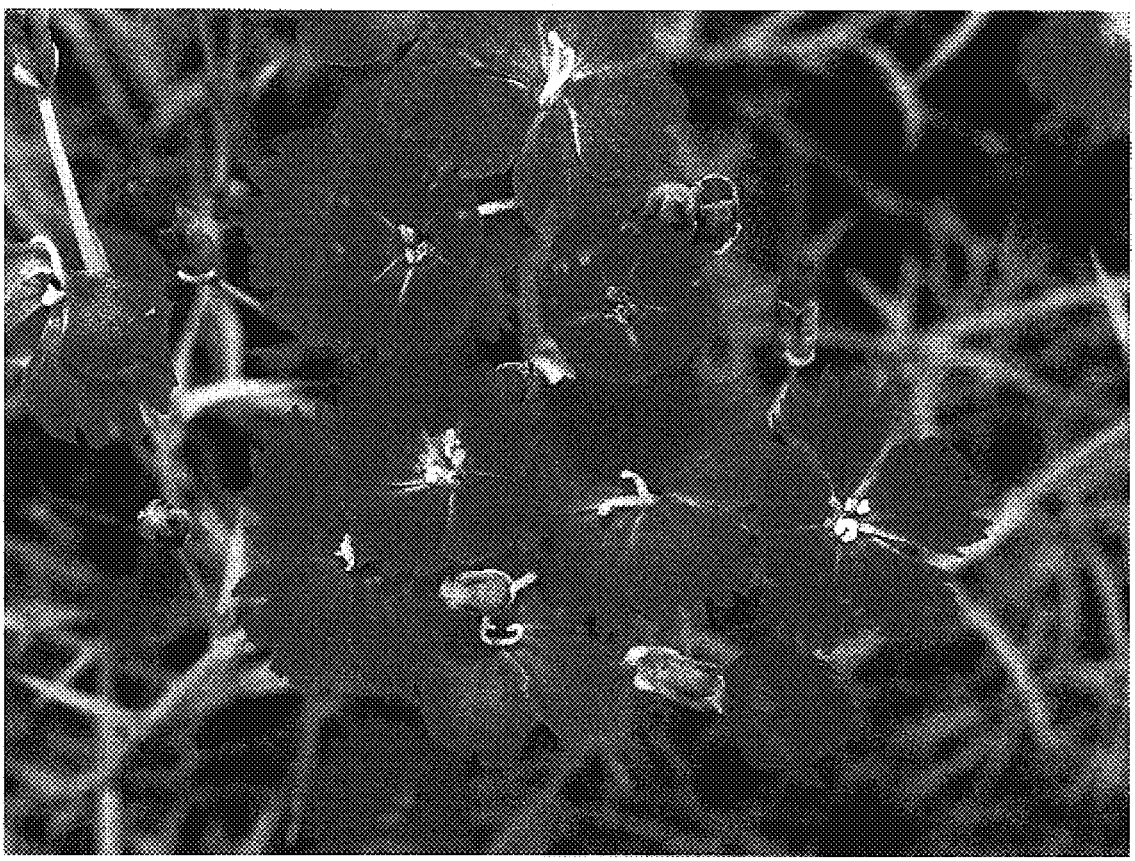

The drawing labeled as FIG. 2 depicts a close-up view of the flowers.

All drawings were made of plants grown in open ground in Raleigh, N.C. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'WICKED WITCH'. Data was collected in spring from 3 inch container plants that had been grown outdoors partially in shade houses in Raleigh, N.C. The color determinations are in accordance with the 2001 edition of the Royal Horticultural Society Colour Chart of the Royal Horticultural Society, London, England, except where general color terms of ordinary dictionary significance are used. No chemicals were used to treat the plants. Growing conditions are typical to other *Dianthus*.

Botanical classification: *Dianthus* 'WICKED WITCH'.
Species: *gratianopolitanus*.
Common name: Dwarf carnation.
Commercial classification: Perennial *dianthus* or Cheddar pinks
Type: Perennial.
Use: Used as a flowering plant for pots and containers.
Parentage: 'WICKED WITCH' is a sport arising from a crop of *Dianthus* 'Feuerhexe'.
Plant description:
- *Bloom period.*—Spring and again in the autumn.
- *Plant habit.*—Mat forming, herbaceous perennial.
- *Plant dimensions at 6 months.*—15 cm to 20 cm in height and width.
- *Plant hardiness.*—Hardy to Zone 3.
- *Root system.*—Fibrous.
- *Propagation.*—Basal cuttings.
- *Cultural requirements.*—Grow in full sun, with moderate water, and well-drained, moderately fertile soil.
- *Diseases and Pests.*—Susceptible to known *Dianthus* pests and disease but no other susceptibilities to pests or disease are known to the inventor. Like its parent 'Feuerhexe', it is very tolerant of heat, drought, and other stressful growing conditions which gives it the ability to withstand attack from pests and diseases more readily than many other perennial *dianthus*.
- *Time and temperature needed to produce a rooted cutting.*—2 weeks are needed to produce roots on cuttings using a mist propagation unit with bottom heat of 20° Centigrade, and a minimum air temperature of 15° Centigrade.
- *Crop time.*—An average of 2–4 months is needed to produce a finished 10 cm container size plant from a well-rooted cutting.

Stem:
- *Shape.*—Terete.
- *Color.*—120D from waxy deposits; 137B when wax is rubbed off.
- *Dimensions.*—80 mm to 90 mm in length, 1 mm to 2 mm in width.
- *Internode length.*—3 mm to 10 mm for non-flowering shoots; up to 50 mm for flowering shoots.
- *Surface.*—Glabrous and glaucous.
- *Node color.*—144A.
- *Node dimensions.*—2 mm in length and 3 mm in width.
- *Branching.*—Numerous basal breaks.

Leaves:
- *Type.*—Evergreen.
- *Shape.*—Linear.
- *Dimensions.*—24 mm to 45 mm in length and 3 mm to 4 mm in width.
- *Division.*—Simple.
- *Apex.*—Acute.
- *Base.*—Decurrent and somewhat perfoliate.
- *Color* (*abaxial and adaxial surfaces*).—122B to 122C.
- *Venation.*—Not prominent; very finely reticulate upon 10× magnification.
- *Margins.*—Appears entire, but very finely serrulate upon close inspection.
- *Attachment.*—Sheathing.
- *Arrangement.*—Opposite and decussate.
- *Fragrance.*—None.

Inflorescence:
- *Form.*—Cymose.
- *Quantity of flowers per stem.*—1 to 2.
- *Type.*—Salverform, single, symmetrical (actinomorphic).
- *Length* (*including pedicel and calyx*).—30 mm to 60 mm.
- *Diameter.*—25 mm to 30 mm.
- *Fragrance.*—Weakly sweet-scented, clove-like.
- *Anthocyanin color* (*where present*).—71A.
- *Bud color.*—145A to N144A on basal portions; 122B on apical portions.
- *Bud shape.*—Cylindrical.
- *Bud dimensions.*—15 mm in length and 5 mm in width.
- *Petals.*—Description: Persistent, single, overlapping. Number: Mostly 5. Dimensions: 3.0 cm in length, 1.5 cm in width. Margin: Dentate with dentations 3 mm deep. Limb shape: Strongly obovate to obdeltoid/spatulate; upwardly revolute. Surface (upper): Bearing sparsely scattered ciliate to mucronate hairs. Surface (lower): Glabrous Shape: Rounded blade-like "limb" (protruding from the tube of the flower) with a strap-like base, called a "claw" (enclosed within the tube of the flower). Color of petal limb (newly opened flowers, adaxial surface): N66B. Color of petal limb (older flowers, adaxial surface): 61B to 60B. Color of petal limb (new and old flowers, abaxial surface): 67B. Color of petal claw (new and old flowers, both surfaces): 145C.
- *Calyx.*—Dimensions: 17 mm in length and 7 mm in width. Color of tube: 91B. Color of anthocyanin: N77A. Texture (both surfaces): Smooth, glabrous, Calyx fused or unfused: Fused. Number of lobes: 5. Color of lobes: 91B.

*Peduncle.*—Dimensions: 12 mm to 40 mm in length and 7 mm in width. Color: 120D with waxy deposits, 137B underneath waxy layer. Surface: Glaucous.

*Bracts.*—Number of epicalyx bracts: 2 individual bracts (1 pair). Shape of apical lobe of bract: Obtuse. Dimensions: 5 mm in length and 5 mm in width. Color: 137A to 137D. Color of anthocyanin: N77A.

*Bracteoles.*—(Number of bracteoles: 2 individual bracteoles (1 pair). Dimensions: 4 mm in length and 2 mm to 3 mm in width. Apex shape: Acute. Anthocyanin present or absent: Absent.

*Stipules.*—None present.

*Lastingness of flowers.*—Not grown as a cut flower.

*Reproductive organs.*—Number of stamens: 10. Stamen dimensions: 20 mm in length and 0.5 mm in width. Filament color: 72A at apical portion; 192D at basal portion. Number of anthers: 10. Pollen amount: Low to moderate. Pollen color: 192D. Pistil nature: Single pistil dividing in two above ovary. Pistil dimensions: 22 mm in length and 3 mm in width. Number of styles: 2. Style dimensions: 12 mm in length and <0.5 mm in width. Style color: 72A at apical portion; white at basal half. Number of stigmas: 2 Stigma color: White and 72A. Stigma shape: Bifid Height of stigma above petals: 8 mm. Ovary disposition: Superior. Ovary dimensions: 10 mm in length and 3 mm in width. Ovary shape: Cylindrical. Ovary color: 145A.

*Seed.*—None observed.

It is claimed:

1. A new and distinct cultivar of *Dianthus* plant named 'WICKED WITCH' as described and illustrated herein.

* * * * *